US005324303A

United States Patent [19]
Strong et al.

[11] Patent Number: 5,324,303
[45] Date of Patent: Jun. 28, 1994

[54] COMBINED LANCET AND MULTI-FUNCTION CAP AND LANCET INJECTOR FOR USE THEREWITH

[75] Inventors: Bernard Strong, Tarzana, Calif.; Robert Oringer, Hampstead, Canada

[73] Assignee: AMG Medical, Inc., Montreal, Canada

[21] Appl. No.: 7,339

[22] Filed: Jan. 21, 1993

[30] Foreign Application Priority Data

Sep. 25, 1992 [CA] Canada .................................. 2079192

[51] Int. Cl.[5] .............................................. A61B 17/32
[52] U.S. Cl. ........................................ 606/181; 606/182
[58] Field of Search ........................ 606/181, 182, 183; 604/111, 117, 192; 128/770

[56] References Cited

U.S. PATENT DOCUMENTS

| | | | |
|---|---|---|---|
| 3,358,689 | 12/1967 | Higgins . | |
| 4,139,011 | 2/1979 | Benoit et al. . | |
| 4,203,446 | 5/1980 | Hofert et al. . | |
| 4,356,822 | 11/1982 | Winstead-Hall . | |
| 4,449,529 | 5/1984 | Burns et al. . | |
| 4,469,110 | 9/1984 | Slama . | |
| 4,503,856 | 3/1985 | Cornell et al. | 606/182 |
| 4,517,978 | 5/1985 | Levin et al. | 606/182 |
| 4,527,561 | 7/1985 | Burns . | |
| 4,635,633 | 1/1987 | Hufnagle | 606/181 |
| 4,677,979 | 7/1987 | Burns . | |
| 4,738,261 | 4/1988 | Enstrom . | |
| 4,759,363 | 7/1988 | Jensen . | |
| 4,817,603 | 4/1989 | Turner et al. . | |
| 4,889,117 | 12/1989 | Stevens . | |
| 4,895,147 | 1/1990 | Bodicky et al. . | |
| 4,976,724 | 12/1990 | Nieto et al. . | |
| 4,990,154 | 2/1991 | Brown et al. . | |
| 5,074,872 | 12/1991 | Brown et al. . | |
| 5,100,427 | 3/1992 | Crossman et al. | 606/182 |
| 5,207,699 | 5/1993 | Coe | 606/182 |

Primary Examiner—Ralph Lewis
Attorney, Agent, or Firm—Henry R. Lerner

[57] ABSTRACT

A combined lancet and multi-function cap of the disposable type, for use in obtaining blood samples for diagnostic purposes. The lancet includes a needle with a sharp end and an elongated body of plastic material embedding the needle except for its sharp end. The multi-function cap is also made of plastic material and is detachably mounted onto one end of the body to embed the sharp end and keep it sterile until the lancet is used. The multi-function cap includes a ring having a central opening sized to let pass the sharp end of the needle but not the body of the lancet. The multi-function cap also includes a set of legs or a skirt that project from the ring for connecting the same to the mouth of a lancet injector. Thus, the cap also serves as an isolation barrier between the patient's finger and the physical lancet injector. In use, when the multi-function cap is detached from the lancet and is connected to the lancet injector, the ring of the cap extends across the mouth and positively controls the depth of penetration of the lancet in the patient's skin. This ring also serves to lock the needle within the cap after use and thus reduces the danger of accidental finger-stick by a blood contaminated needle. Also disclosed is a lancet injector for use with the above lancet and multi-function cap.

19 Claims, 12 Drawing Sheets

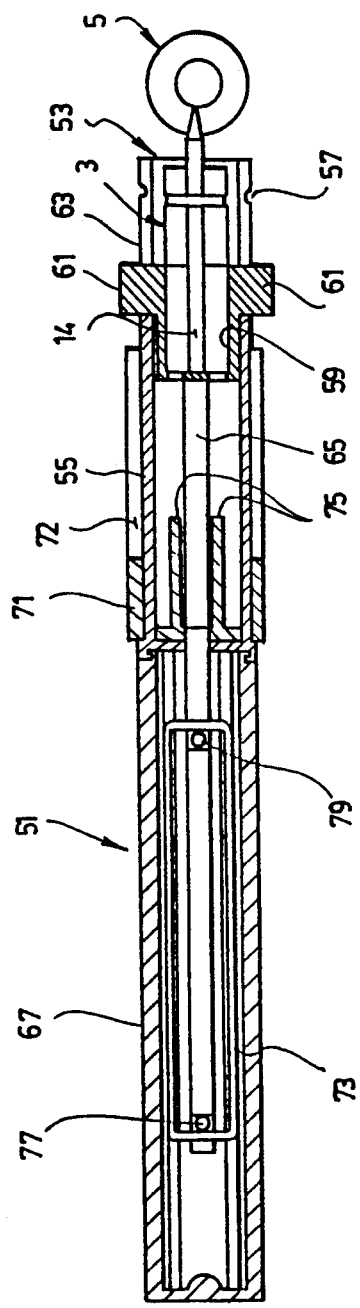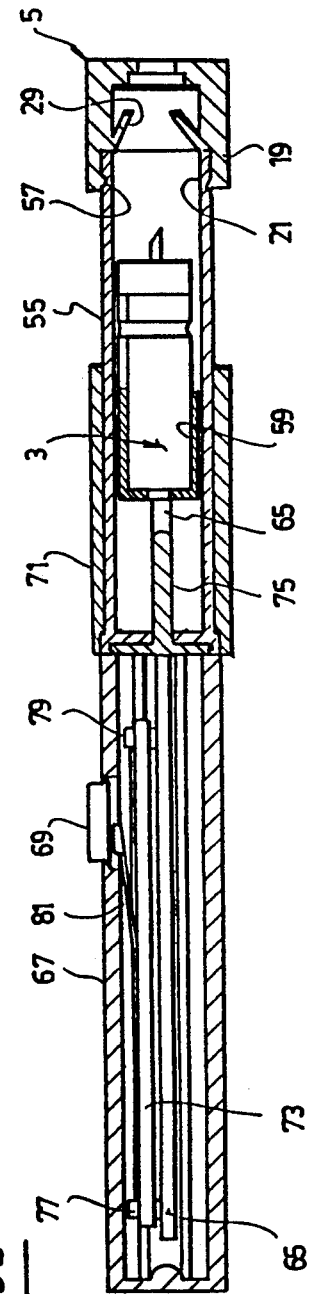

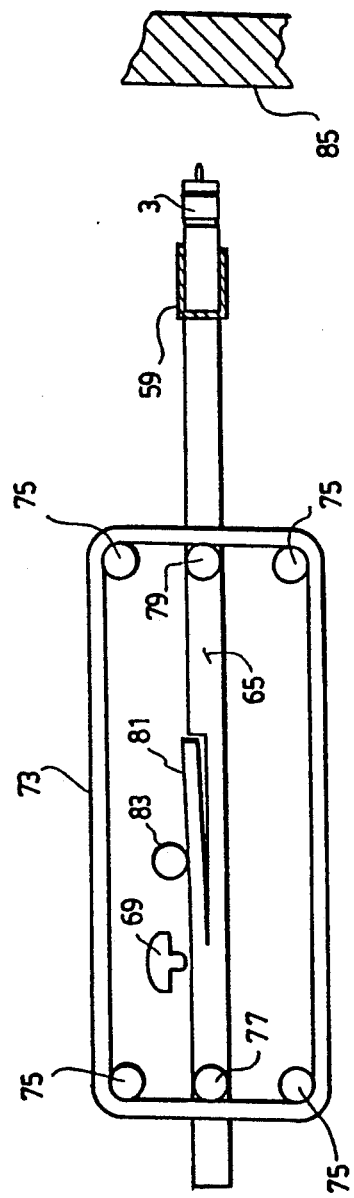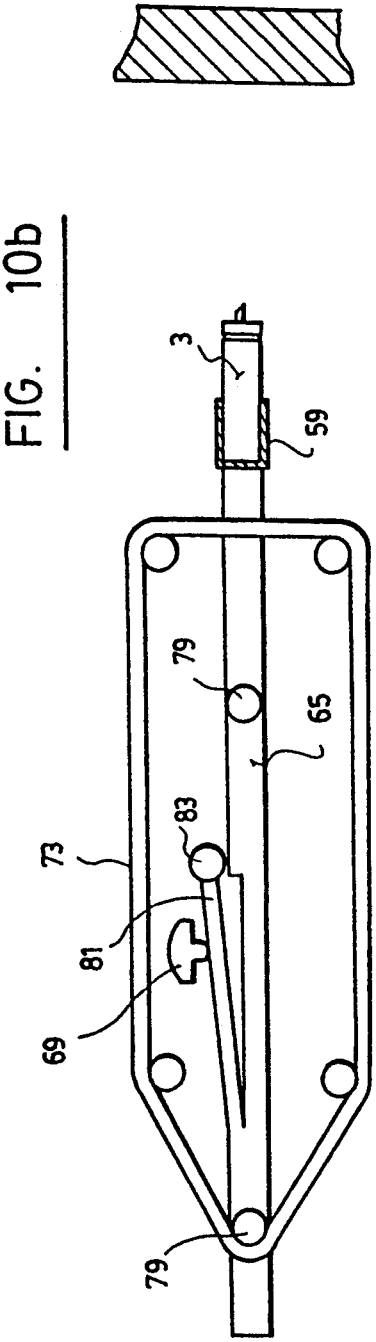
FIG. 10a
FIG. 10b

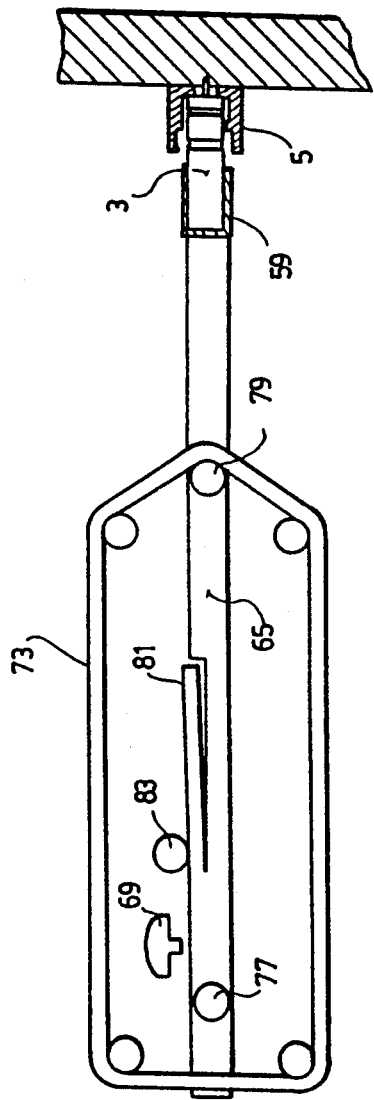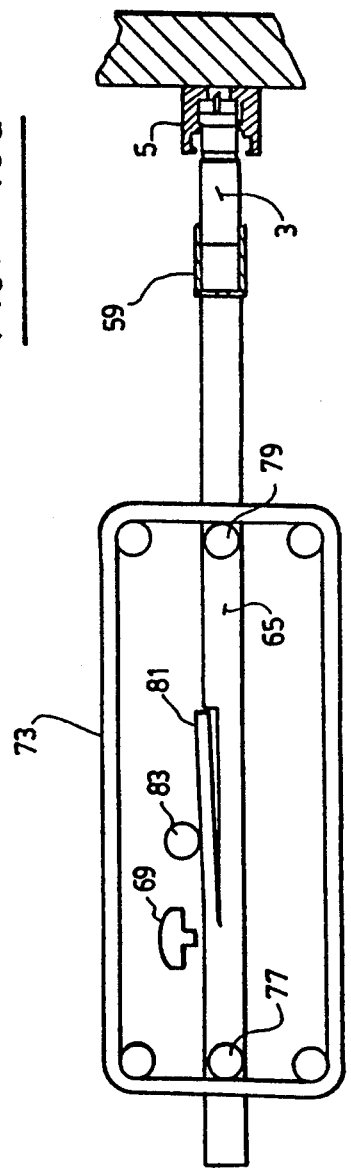

COMBINED LANCET AND MULTI-FUNCTION CAP AND LANCET INJECTOR FOR USE THEREWITH

BACKGROUND OF THE INVENTION a) Field of the Invention

The present invention relates to a combined lancet and multi-function cap (or tip) of the disposable type, for use in obtaining blood samples for diagnostic purposes.

The invention also relates to an improved blood sampling device also known in the trade as a "lancet injector" or "lancing device", that can be used with the combined lancet and multi-function cap according to the invention for obtaining required blood samples in a very safe and accurate manner.

b) Brief Description of the Prior Art

Lancets are well known devices commonly used in the medical field to make small punctures in a patient's skin in order to obtain small samples of blood. Lancets usually comprise an elongated plastic body from which projects a sharpened metal needle covered by a protective cap that is removed before use of the needle to puncture the skin (see, by way of non-restrictive example, U.S. Pat. No. 3,358,689 to HIGGINS).

Lancet injectors are also well known devices that are used to "fire" or project a lancet toward the skin of a patient in order to puncture the same in an accurate, standardized and consistent manner.

Such devices have originally been devised for use by the patients' themselves, who have to puncture their own skin on a regular basis and are afraid or reluctant to do so "manually". However, they are now commonly used by professional medical staff, essentially because they make the duration and depth of penetration of the lancet needle through the skin very short and small and serve to shield the patient from viewing the actual skin piercing act, and thus they minimize pain and trauma associated with the process.

In the recent years, numerous patents have been granted on lancet injectors of different and improved structures. By way of non-restrictive examples, references can be made to the following U.S. Pat. Nos. 4,139,011 to BENOIT et al, 4,449,529 to BURNS et al, 4,469,110 to SUAMA, 4,527,561 to BURNS, 4,677,979 to BURNS, 4,738,261 to ENSTROM, 4,889,117 to STEVENS, 4,895,147 to BODICKY et al, 4,976,724 to NIETO et al, 4,990,154 to BROWN et al, 5,074,872 to BROWN et al.

A brief review of these patents shows that all the known lancet injectors use metallic coil or leaf springs to push the lancet forward upon actuation and then retract it immediately in order to minimize pain sensation (see, for example, U.S. Pat. Nos. 4,203,446; 4,469,529; 4,527,561; 4,677,979 and 4,889,117).

Some known lancet injectors are also provided with means, usually in the form of a screwable ring or separable multiple sized adaptor caps, to control and adjust the depth of penetration of the needle of the lancet (see, for example, U.S. Pat. Nos. 4,469,110 and 4,895,147).

Some other known lancet injectors are provided with means for allowing ejection of the lancet after use without having to seize it with the fingers to do so. Such is achieved either by use of mechanical ejecting means (see U.S. Pat. No. 4,976,724) or by use of a separate disposable isolation cap operatively connected to the lancet in such a manner as to act as a protective hood for its needle (see U.S. Pat. Nos. 4,990,154 and 5,074,872). The basic idea behind this last generation of lancet injectors is essentially to make them safer in use by the professional medical staffs who are more and more concerned with the risk of disease transmission in the case of accidental puncture with a used lancet and resultant exposure to contamination through the trace of blood left on the used lancet.

OBJECTS OF THE INVENTION

A first object of the present invention is to provide a combined single-use, disposable lancet and multi-function cap, which is preferably made in one moulding, and in which the multi-function cap is so devised as to be useful in four separate and distinct functions. These four separate and distinct functions are as follows:

First function: The multi-function cap shall serve as a protective cap (or sealed barrier) to keep the sharp needle of the lancet protected and sterile after moulding and prior to being twisted off to reveal the needle for actual use.

Second function: The multi-function cap shall serve as an isolation cap (or physical intermediary) when the lancet is being used with a lancing device such that no physical part of the actual lancing device itself may come into contact with the target area of the patient's skin from which blood is to be drawn. Only the multi-function cap makes physical contact with the target area of the patient's skin from which blood can be drawn.

Third function: The multi-function cap shall serve as a means of controlling depth of penetration when the lancet is being used with a lancing device (injector) such that the user has variable options of the depth to which the lancet may be allowed to penetrate the skin.

Fourth function: The multi-function cap shall serve as a protective cap (or locking hood) to cap and permanently lock the used sharp lancet needle "within" the cap immediately upon use of the lancet, thus serving to protect users and medical professionals against risk of accidental finger puncture once the lancet has been used (fired).

Simultaneously, the multi-function cap serves to prevent the lancet from being fired, accidently, for a second time.

The fact that the multi-function cap is not only acting as a protective cap to keep the needle sterile before use, but also as an isolation cap, a depth penetration barrier and a locking needle hood, is of a great interest as it eliminates the need for an extra isolation cap and it economizes both in manufacturing cost and in required amount of plastic material. The weight of the extra isolation cap presently being used with devices as disclosed in U.S. Pat. Nos. 4,990,154 and 5,074,872 being presently approximately 0.25 grams, ultimate worldwide adoption of the invention by the 50 million known diabetic patients would in practice result in an annualized savings in plastics materials in excess of 5,000 tons.

A second object of the invention is to provide a blood sampling lancet injector for use with the above mentioned combined lancet and multi-function cap, which lancet injector is devised to reduce the danger of accidental finger-stick from a "used" blood contaminated lancet needle, thanks to the presence of ejection means which automatically eject the lancet in concert with the multi-function cap that firmly grips onto the lancet at a predetermined position where it acts as a protective locking hood for the needle after the device has been "fired" and the used lancet is ejected and discarded.

A third object of the invention is to provide a blood sampling lancet injector of the above type, which, thanks to the multi-function cap of the combined lancet and multi-function cap used therewith, allows for easy regulation of the depth of skin penetration in a positive and reliable manner for purposes of obtaining an ample and optimum volume blood droplet.

It is known that normal average desirable penetration to produce sufficient blood for glucose content purposes as required for instance by most diabetic patients is around 0.040". For young children, a penetration 0.025" to 0.030" is sufficient and provides less discomfort while for some adults who have a thicker than usual epidermis, up to 0.090" may be needed to produce an ample blood droplet. The invention provides for all penetration depths within these two extremes with a lancet having just one given needle length, the required depth being easily adjusted in a very reliable manner by mere rotation of a depth indicator forming part of the multi-function cap and provided with an easy-to-read scale giving different comfort depth value, in order to reduce as much as possible discomfort.

A fourth object of the invention is provide an improved, low cost blood sampling lancet injector which eliminates the use of metallic springs, and uses instead an elastomeric band which is suitably restrained at four points so as to provide a unique two-way, well cushioned prime mover providing both for very rapid skin piercing and speedy withdrawal of the needle, said rapid speed movements of which serve to minimize patient discomfort.

A fifth and last object the invention is to provide a blood sampling lancet injector which incorporates each and all of the above mentioned features and thus:

is much less complicated than the poor art devices which require the use of metallic springs that are far more costly than the elastomeric band used herein:

Is much safer than the prior art devices which do not provide for disposable isolation caps, the invention not only obviating cross-contamination, but also allowing for instant regulation of the depth of skin penetration and protective hooding and locking of the needle after use to eliminate the possibility of "second firing" without employing any extra components; and is much less expensive to manufacture than the prior art devices which, for most, require costly assembly operations that may include sonic welding, gluing and-/or screwing, the invention, in complete contrast, providing for rapid low cost assembly with all components suitably shaped to rapidly click together either by hand or a robotic assembly machine.

SUMMARY OF THE INVENTION

In accordance with a first aspect of the invention, there is provided a combined lancet and multi-function cap of the type comprising:

a) a lancet including a needle having a sharp end, and an elongated body of plastic material embedding this needle expect for its sharp end that projects from one end of this body over a given length, the elongated body having at least one longitudinal rib; and b) an isolation cap also made of plastic material, this cap being detachable mounted on the one end of the body to embed the sharp end of the needle and keep it sterile until the lancet is used.

This basic combination distinguishes over those already known in the art in that the isolation cap is a multi-function cap and comprises:

a ring having an inner face, an outer face and a central opening sized to let pass the sharp end of the needle but not the one end of the body of the lancet; and means for use to properly position the ring with respect to a lancet injector having a mouth through which the lancet may be inserted and subsequently projected out, in such a manner that the central opening of said ring is aligned with the sharp end of the needle.

To achieve such a penetration, the ring has such a thickness and a shape as to let the sharp end of the needle pass through the central opening and penetrate the skin of the patient's finger in contact with the outer face of the ring.

In use, when the multi-function cap is detached from the lancet and is connected to the mouth of the lancet injector, the ring of the cap extends across this mouth and positively controls the depth of penetration of the lancet in the patient's skin.

The above-mentioned means for use to properly position the ring with respect to the lancet injector preferably consists of connection means integral to and projection from the ring in the direction of its inner face, for connecting the cap to the lancet injector across the mouth of the same.

In accordance with another aspect of the invention, there is also provided a lancet injector for use with the above combined lancet and multi-function cap.

This lancet injector basically comprises:

a lancet receiving sleeve having a longitudinal axis and a mouth at one end through which the lancet may be inserted and subsequently projected out;

a lancet holder slidably mounted within the sleeve, the holder being sized and shaped to receive the lancet and to cooperate with the longitudinal rib of this lancet to prevent it from rotating about the longitudinal axis;

means to prevent the lancet holder from rotating within the lancet receiving sleeve, these means comprising a gripping wings radially projecting from said lancet holder and slidably engaged within longitudinal slots provided for this purpose within the sleeve, the gripping wings projecting radially outwardly from the sleeve through the longitudinal slots;

a central shaft integrally projecting from the lancet holder in a direction opposite to the mouth, the central shaft being coaxial with the longitudinal axis and projecting out of the lancet receiving sleeve;

elastic means mounted in a housing connected to the lancet receiving sleeve opposite the mouth thereof to project forward the central shaft and lancet holder upon pressing of release button externally mounted on the housing, these elastic means being energized and the release button triggered in operative position every time the lancet holder is manually moved within the sleeve by the gripping wings; and a sleeve-shaped ejector slidably mounted externally onto the lancet receiving sleeve, the ejector having longitudinal slots positioned to make it movable without being stopped by the gripping wings and means to engage the lancet with the lancet holder and being manually movable toward the mouth of the lancet receiving sleeve to push the lancet out of the lancet holder and to detach and throw out the multi-function cap connected and locked thereto without having to put the fingers on the cap to remove the used lancet from the lancet injector.

The invention and its numerous advantages will be better understood upon reading the following non-restrictive description, given with reference to the accompanying drawings.

BRIEF DESCRIPTION OF THE DRAWINGS

FIG. 9a is top cross-sectional view of the lancet injector shown in FIG. 5, when the combined lancet and cap is loaded therein;

FIGS. 9b to 9e are side-elevational, cross-sectional views of the lancet injector as it is shown in FIG. 6, showing the position of the multi-function cap when it is installed, the position of the lancet when the injector has been fired, the position of this lancet after the injector has been used and the way the lancet can be ejected together with the multi-function cap, respectively;

FIGS. 10a to 10d is a diagrammatic representation of the elastomeric band used as lancet projecting means in the lancet injector shown in FIGS. 5 to 9, at different stages of use;

DESCRIPTION OF PREFERRED EMBODIMENTS

Figure 1:
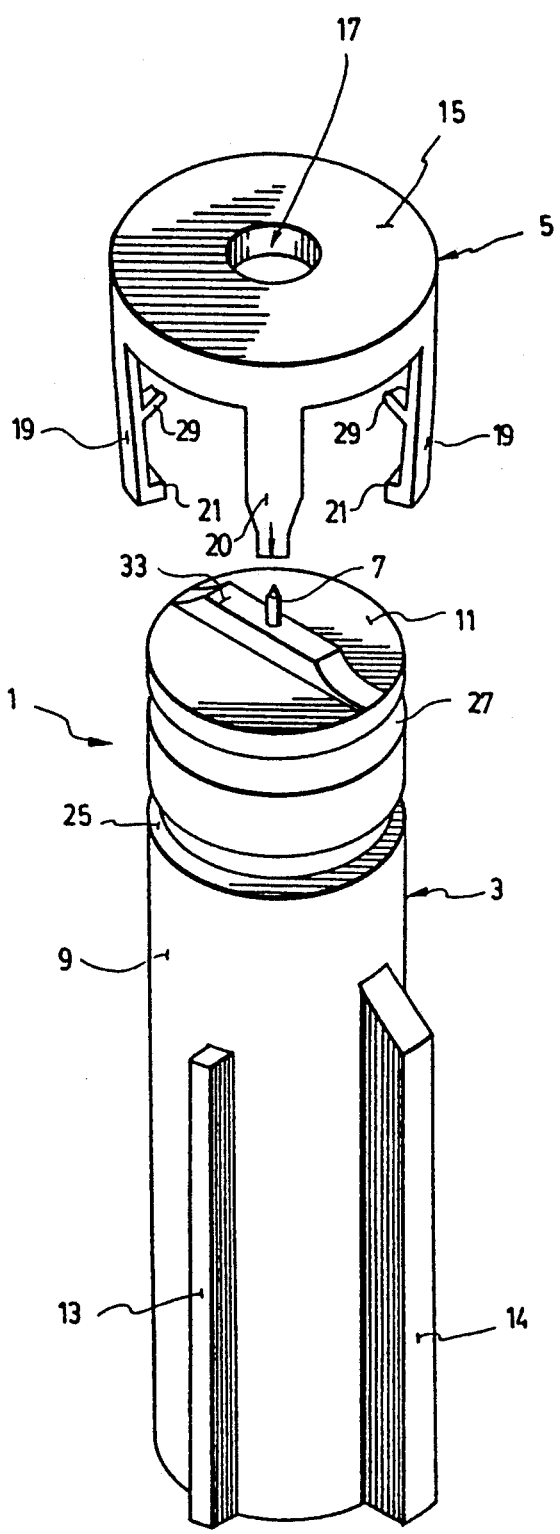
FIG. 1 is a perspective view of a combined lancet and multi-function cap according to the invention, showing the multi-function cap in a position to control depth of penetration of the lancet.

FIGS. 1 to 3 and 11 to 13 show a combined lancet and multi-function cap 1 according to a first embodiment of the invention. This combination 1 is made up of a lancet 3 and a multi-function cap 5. The lancet 3 includes a needle 7 having a sharp end, and an elongated body 9 made of plastic material, which embeds the needle except for its sharp end that projects from one end 11 of the body over a given length. As is clearly shown, the elongated body is made with a plurality of longitudinal ribs 13 to make it easier to grasp and handle, and easier to mount and lock in a lancet injector 51 as is shown in FIGS. 5 to 9.

Figure 3:
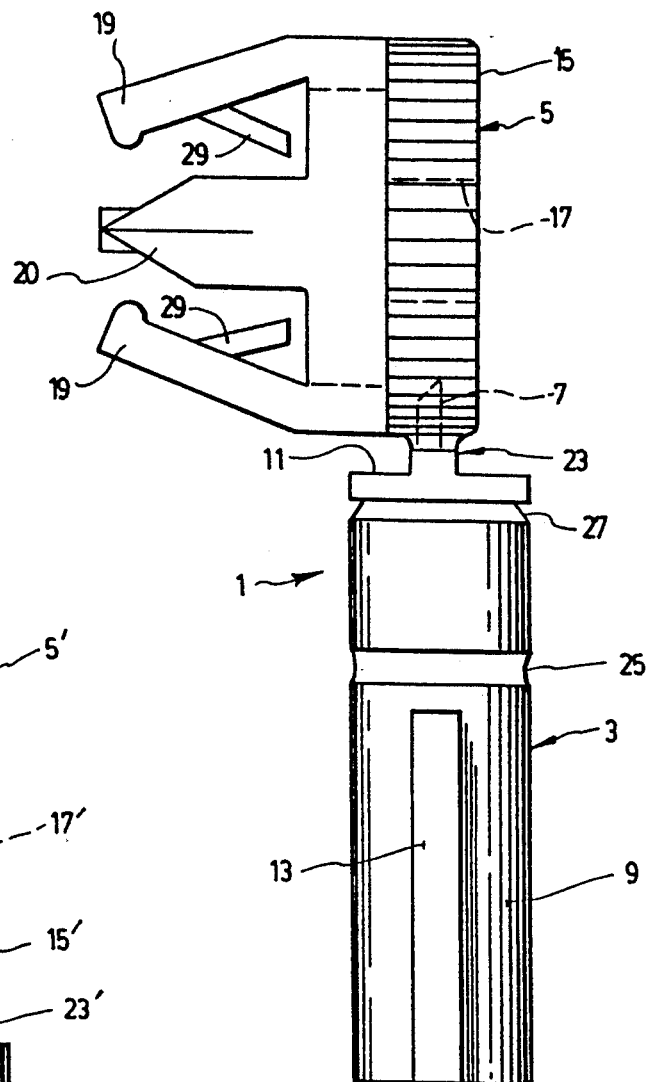
FIG. 3 is a side elevational view of the combined lancet and multi-function cap of FIGS. 1 and 2, showing the multi-function cap as it is moulded at one end of the lancet to embed the needle and keep it sterile until it is used.
Figure 4:
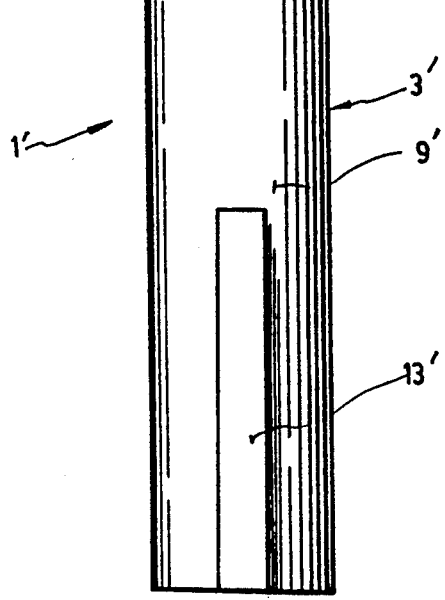
FIG. 4 is a view similar to FIG. 3, showing a combined lancet and multi-function cap according to the invention with a tip of structure different from above.
Figure 5:
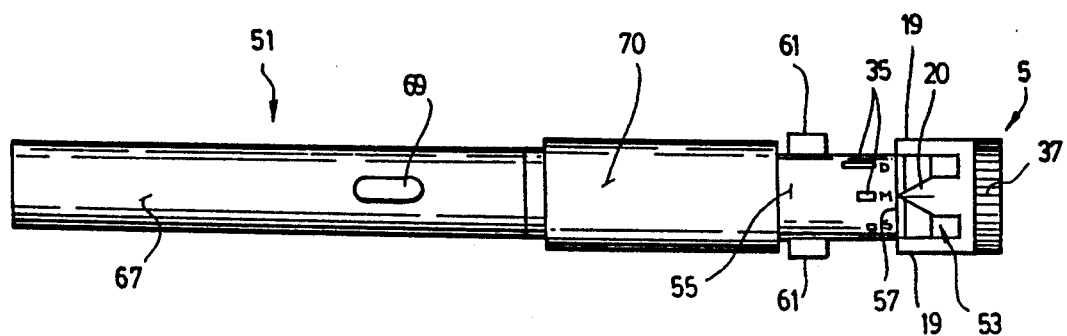
FIGS. 5 and 6 are top and side elevational views of a lancet injector for use with the combined lancet and multi-function cap of FIGS. 1 to 3, showing the multi-function cap mounted in operative position to control depth of penetration.
Figure 6:
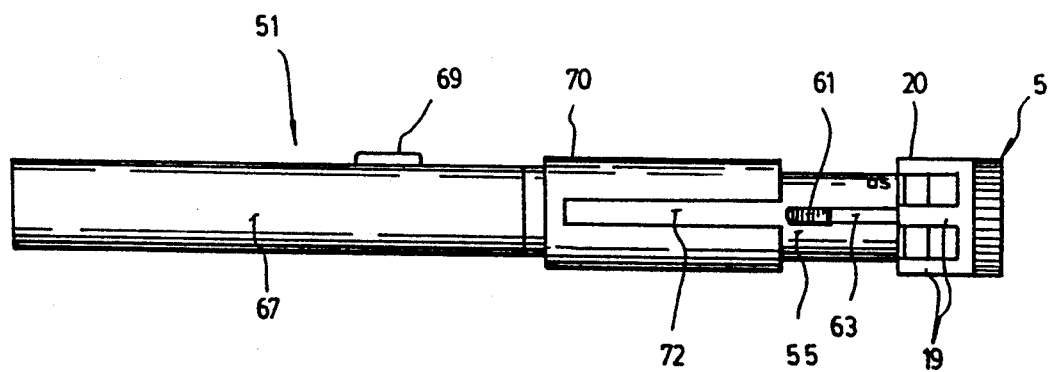

This multi-function cap 5 is also made of plastic material. This cap is detachably mounted on the one end 11 of the body 9 as is shown in FIG. 3 to embed the sharp end of the needle 7 and keep it sterile until the lancet is used.

The multi-function cap 5 comprises a ring 15 having an inner face, an outer face and a central opening 17 sized to let pass the sharp end of the needle 7 but not the one end 11 of the body 9 of the lancet. The ring 15 has a shape and a thickness that are selected to let the sharp end of the needle 7 pass through the central opening 17 and penetrate the skin of a patient's finger in contact with the outer face of the ring, while, at the very same time, the one end 11 of the body 9 bears against the inner face of the ring 15.

The multi-function cap 5 also comprises means for use to properly position the ring with respect to a lancet injector 51 as shown in FIGS. 5 to 9, having a mouth 53 through which the lancet 5 may be inserted and subsequently projected out to penetrate in the skin of the patient's finger. Of course, such means must be devised in such a manner that the central opening 17 of the ring 15 is aligned with the sharp end of the needle 7 when the same is in the injector 51.

In accordance with a particularly preferred embodiment of the invention, these means preferably consist of connection means integral to and projecting from the ring 15 in the direction of the inner face of this ring, for use to connect whenever desired, the multi-function cap 5 to the mouth of the lancet injector 51.

In the first embodiment of the invention, shown in FIGS. 1 to 3 and 11 to 13, the connection means consist of at least three and preferably four legs 19 symmetrically positioned around the ring 15. These legs 19 project from the ring in the direction of the inner face of this ring and have resilient ends 21 snappable into a groove 57 provided for this purpose on the lancet injector 51 near the mouth 53 of this injector.

The lancet 3 and multi-function cap 5 are preferably made of the same plastic material and moulded together to form an integral structure moulded onto the needle 7, with the body 9 of the lancet 3 radially projecting from the ring 15 of the cap 5, as is shown in FIG. 3. In such a position, the body 9 and ring 15 are integrally connected by a very short stem 23 of reduced diameter that is coaxial to the needle 7 and sized to make the multi-function cap 5 easily detachable from the body 9 by twisting and pulling, to release the sharp end.

When the multi-function cap 5 is detached from the lancet 3 and is connected to the lancet injector 51, the ring 15 of the cap extends across the mouth 53 and positively controls the depth of penetration of the lancet 3 in the patient's skin, as will be explained hereinafter.

Referring back to FIGS. 1 to 3, the body 9 of the lancet 3 advantageously comprises a first peripheral groove 25 that extends parallel to its one end 11, this groove being sized to be snapped by the resilient ends 21 of the legs 19. This first peripheral groove 25 is positioned along the body 9 at such a distance that when the resilient ends 21 of the legs 19 are snapped into the first groove 25, the ring 15 of the multi-function cap 5 extends past and over the sharp end of the needle 7 that projects from the one end 11 of the body 9 of the lancet 3 as is shown in FIGS. 2 and 9e, thereby preventing accidental finger-sticks with this sharp end.

In accordance with a particularly preferred embodiment of the invention, the body 9 of the lancet 3 also comprises a second peripheral groove 27 extending parallel to the first grove 25 between this first groove and the one end 11 of the body 3, and each of the legs 19 of the multi-function cap 5 comprises a small restraining leaf 29 projecting towards the center of the central opening 17 of the ring 15 of the cap. As is shown in FIG. 9d, the leaves 29 are of such a length as to engage and lock into the second groove 27 of the body 9 to prevent the lancet 3 from moving out from the cap 5 after the lancet has been projected toward the inner face of the ring 15 by the lancet injector 51 and has bounded back at a safe distance where the sharp end of the needle 7 does not project anymore from the outer face of this ring. This feature and its advantages will be further explained hereinafter.

Figure 12:
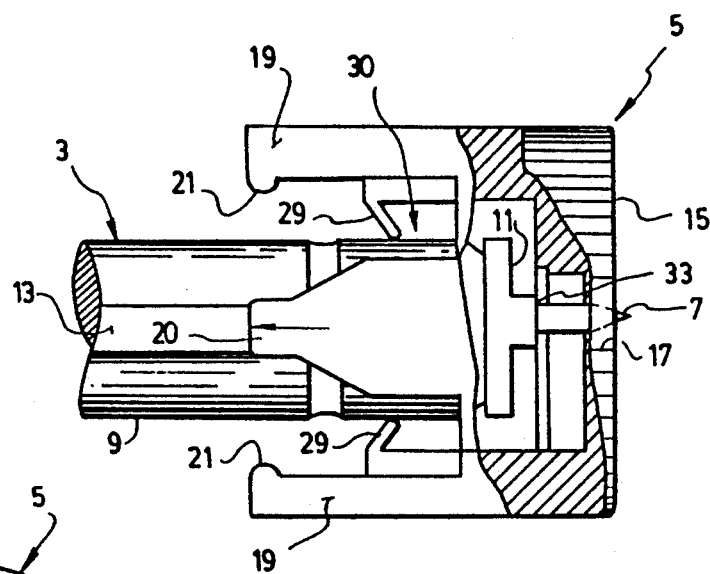
Figure 13:
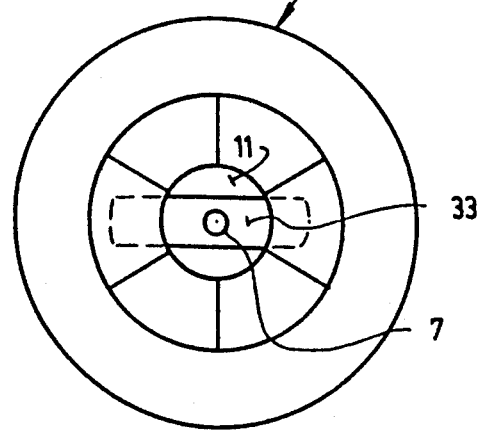
Figure 14:
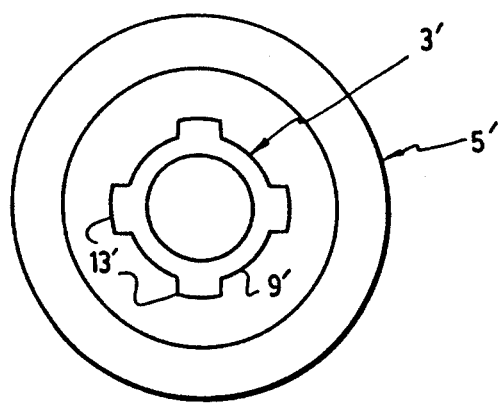
FIGS. 14 to 16 are bottom, side elevational and top plan views of the combined lancet and multi-function cap shown in FIG. 4, the side elevational view having cut-away portions.
Figure 15:
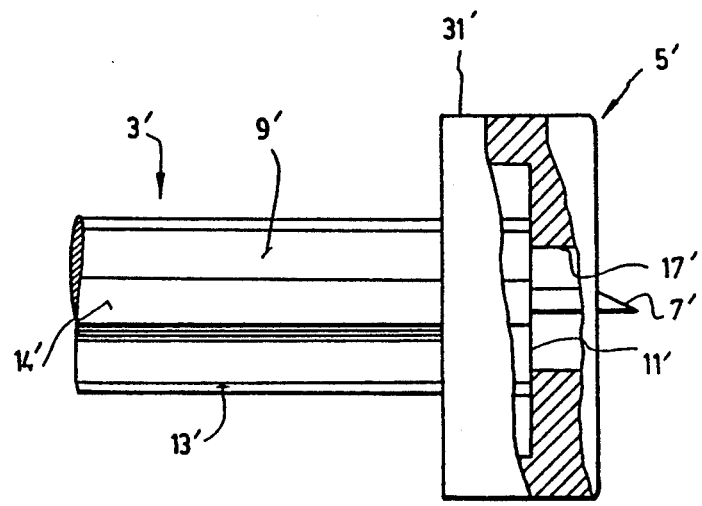
Figure 16:
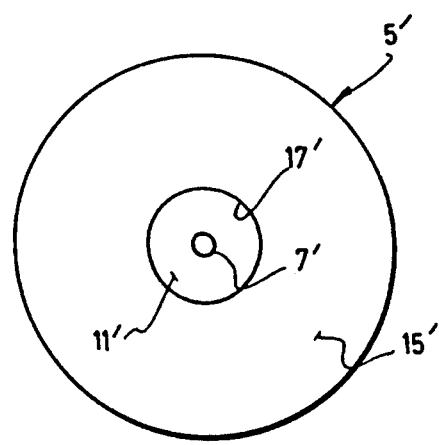

The spaces between the peripheral rearward edge of the ring 15 and the legs 19 of the multi-function cap define a plurality of apertures 30 acting as viewing windows to make it possible for someone to check whether the lancet is engaged and locked by the restraining leaves 29, such an engagement being indicative that the lancet has been used once and is to be discarded (see FIG. 12).

FIGS. 4 and 14 to 16 show a combined lancet and multi-function cap 1' according to a second embodiment of the invention, which is very similar to the first one, except for the structure of the connection means that form part of the multi-function cap 5' and are used for connecting the cap 5' to the mouth 53 of the lancet injector 51. The difference in structure between this cap 5' and the one previously disclosed reduces its use to two separate and distinct functions (as opposed to the three functions of the first embodiment). For the purpose of simplicity, the same reference numerals as above, have been used to identify the same structural elements, with a distinguishing prime (').

Figure 7:
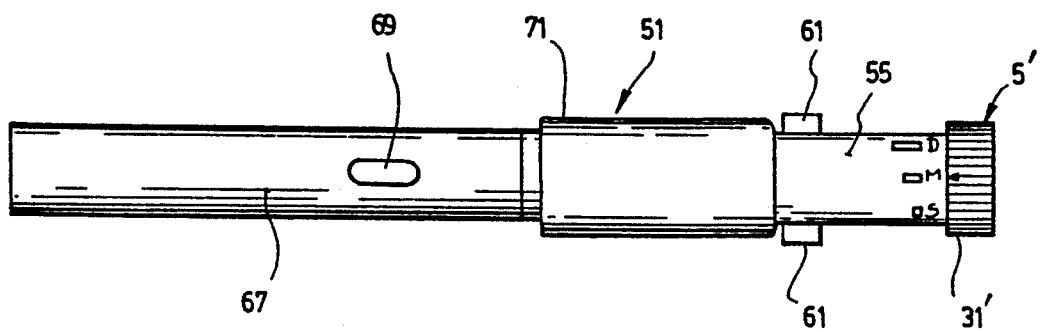
FIGS. 7 and 8 are front and side elevational views of the injector device of FIGS. 5 and 6, showing it in use with the combined lancet and multi-function cap of FIG. 4.
Figure 8:
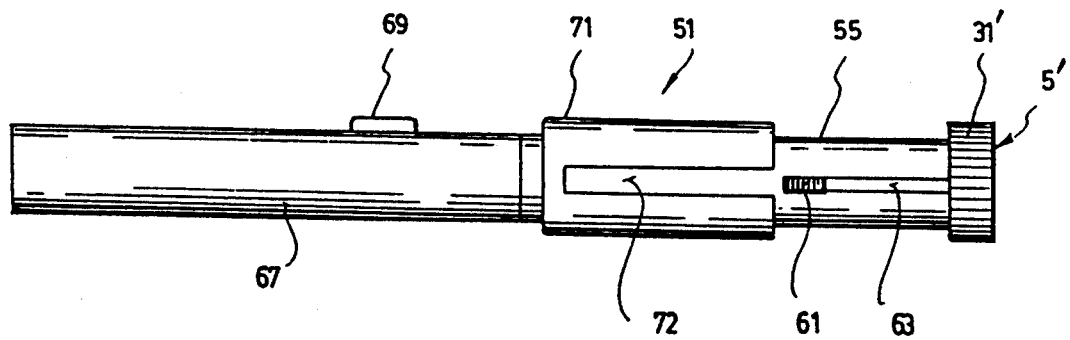

In this second embodiment, the connecting means consists of a peripheral skirt 31' integrally projecting from the ring 15', the skirt 31' being sized and shaped to snugly fit onto the mouth 53 of the injector device 51 as is shown in FIGS. 7 and 8.

Referring now to FIGS. 5 to 9, the lancet injector 51 that can be used with the combined lancet and multi-function cap 1 or 1' disclosed hereinabove, basically comprises a lancet receiving sleeve 55 having a longitudinal axis. This sleeve 55 defines at one end, the mouth 53 through which the lancet 3 or 3' may be inserted and subsequently projected out. The device 51 also comprises a lancet holder 59 slidably mounted within the sleeve. This holder 59 is sized and shaped to receive the lancet 3 or 3', and to cooperate with one of the longitudinal ribs of this lancet, namely these numbered 14, 14' in the drawings, to prevent it from rotating about the longitudinal axis.

Means are provided to prevent the lancet holder from rotating within the lancet receiving sleeve. These means consists of a pair of gripping wings 61 radially projecting from the lancet holder 59 and slidably engaged within longitudinal slots 63 provided for this purpose in the sleeve 55, these gripping wings 61 projecting radially outwardly from the sleeve through these longitudinal slots 63 as is showing FIGS. 5 to 9.

The lancet injector 51 further comprises a central shaft 65 integrally projecting from the lancet holder 59 in a direction opposite to the mouth 53. This central shaft 65 is coaxial with the longitudinal axis of the sleeve 55 and projects out of this sleeve.

Elastic means are mounted in a housing 67 connected to the lancet receiving sleeve 55 opposite to the mouth 53, in order to push forward the central shaft 65 and the lancet holder 59 connected thereto upon pressing of a release button 69 externally mounted on the housing. These elastic means are devised to be energized and the release button triggered in operative position every time the lancet holder 59 is manually moved within the sleeve 55 by means of the gripping wings 61.

The lancet injector 51 also comprises a sleeve-shaped ejector 71 externally mounted in a slidable manner onto the lancet receiving sleeve 55. The ejector 71 has longitudinal slots 73 positioned to make it movable without being stopped by the gripping wings 61. It also has ejecting means 75 in the form of short stems projecting opposite to the central shaft 65. This ejector 71 is manually movable toward the mouth 53 of the lancet receiving sleeve 55 to push the lancet 3 or 3' out of the lancet holder 59 and to detach and throw out the multi-function cap 5 or 5' connected thereto without having to touch this tip with the fingers.

Any kind of elastic means may be used within the housing 67 provided that they may project the central shaft 65 forward upon pressing on the release button 69.

However, in accordance with a preferred embodiment of the invention, this elastic means preferably consists of an elastomeric band 73 (see FIGS. 9 and 10) which is suitably constrained between four points 75 and within which the center shaft 65 connected to the lancet holder 59 is permitted to move bi-laterally in such a manner that movement of this shaft in a rearward direction gives rise to a tensioning of the band which is then locked in position when the potential energy is stored (see FIG. 10b). When the shaft 65 is released, the potential energy stored in the band 73 produces the requisite kinetic energy to rapidly accelerate the shaft and the connected lancet until the lancet 3 impacts the disposable multi-function cap 5 the effective thickness of which at the point of contact with the lancet 3 serves to regulate the depth of skin penetration of the needle 7 (see FIG. 10c). At the time of impact, the elastomeric band 73 stretches for a second time due to the pressure exerted upon its forward end as the inertia of the moving central shaft 65 causes it to move past its normal rest position to which the band then rapidly returns it, thus withdrawing the needle 7 (see FIG. 10d). The very high speeds of penetration and withdrawal coupled with the intrinsic cushioning of the elastomeric band 73 provide help to minimize any sensation of pain.

In greater details, the elastomeric band 73 is wrapped under slight tension around four restraining points 75 that are integral to the housing 71 and situated at the four corners of a rectangle having a main axis coaxial with the longitudinal axis of the central shaft 64. Within the periphery of this rectangle stand a rear pin 77 and a front pin 79 that radially project from the shaft 65 so as to just make contact with the small sides of the elastomeric band 73. The shaft 65 is suitable constrained by guides (not shown) so that it can only move bi-laterally.

When the shaft 65 is pulled to the left as shown by arrow X1 in FIGS. 9b and 10b, such occurring when the lancet holder 59 is moved in the same direction by the wings 61, the tension within the elastomeric band 73 is considerably augmented due to stretching.

A self-tensioned detent 81 is provided on the central shaft. This detent 81 is integral to the central shaft 65 and projects therefrom radially outwardly. Of course, this detent 81 is moved together with the shaft when the same is moved to the left, and then vertically upwardly until it is locked behind a detent stop 83 that is positioned into the housing in such a manner as to extend across the detent 81 and lock the central shaft 65 in a rearward position where the rear pin 79 of the central shaft presses against the elastomeric band 71 and is biased by the same, and the lancet holder 59 extends within the lancet receiving sleeve 55 away from its mouth 53 (see FIGS. 9b and 10b).

In such a position, potential energy is stored in the device and is retained therein.

When the release button 69 is depressed, detent 81 is caused to move downwards, thus causing the shaft 65 to unlock as the self-tensioned detent 81 escapes from behind the detent stop 83. This releases the potential energy stored in the device, which then fires by moving rapidly to the right as shown in FIG. 10c. Upon firing, the shaft 65 moves rapidly in the direction of arrow Y until such time as its forward motion is arrested due to the lancet 3 striking the inner surface of the isolating tip 5 and simultaneously piercing the patient's skin 85 to a predetermined depth which is controlled by the effective thickness of the ring 15 of the multi-function cap 3, whereupon the lancet instantly commences to retract in the direction shown by arrow X3 in FIG. 10d by virtue of the pressure then exerted by the elastomeric band 73 on the front pin 79, such pressure being due to the inertia of the shaft 65 causing it to overshoot its original retracted position depicted in FIG. 10a.

Figure 2:
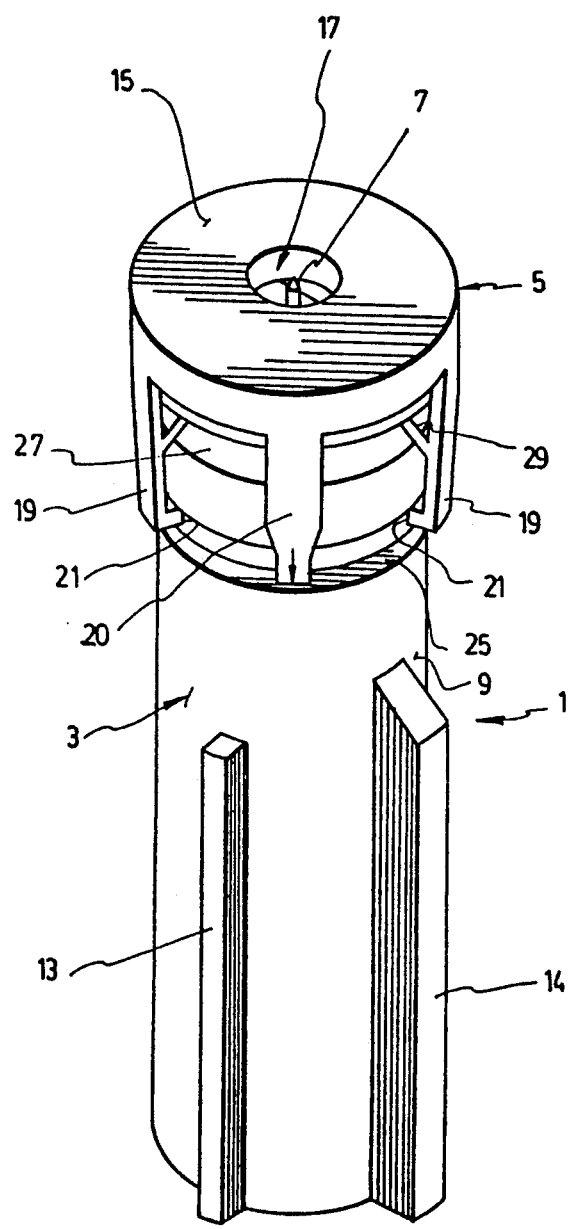
FIG. 2 is a perspective view of the combined lancet and multi-function cap of FIG. 1, showing the multi-function cap snapped onto the lancet to control depth penetration of the needle during use of this lancet and then to protect, lock and isolate the needle after use to prevent accidental puncture and eliminate the possibility of second firing.

If a combined lancet and multi-function cap 1 as shown in FIGS. 1 to 3 is used, the lancet 3 will only be permitted to partially retract when the shaft 65 retracts, as this lancet will be retained in a position where the needle 7 of the lancet 3 is below the surface of the multi-function cap 5 due to the restraining leaves 29 which are angled so that they are easily deflected on the forward stroke of the lancet 3 but snap into the retention groove 27 provided on the body 9 of the lancet during the rearward stroke thereby inhibiting further movement and thus partially extracting the lancet 3 from the lancet holder 59.

In this retained position, the lancet 3 blocks viewing through the window-defining apertures 30 so that, by attempting to look through these apertures 30, one may readily determine if the lancet 3 within the device 51 has been used, in which case the windows 30 will be completely obscured.

The rapid retraction of the shaft 65 due to the elastomeric band 73 cause this shaft to slightly overshoot in the reverse direction as its rear pin 77 hits the elastomeric band 73 which then acts as an excellent shock absorber and mechanically projects all the components within the device from undue shock and consequential wear. The shaft 65 then continues to make a number of minor and gradually reducing bilateral oscillations between the two small sides of the elastomeric band 73 as the rear pin 79 and front pin 79 make alternate contact with it and the potential energy within the system is smoothly and completely dissipated.

Thus, pushing by the release button 69 of the detent 81 causes the central shaft 65, the lancet holder 59 and the lancet 3 or 3' mounted therein to be projected forward toward the mouth 53 of the sleeve 55, and then to be pulled back by action of the elastomeric band 73 onto the front pin 79, thereby causing very rapid skin perforation and speedy withdrawal of the needle 7.

In the embodiment shown in FIGS. 1 to 3 and 11 to 13, the one end 11 of the body 9 of the lancet 3 has a radially extending section 33, hereinafter called "truncated section", that projects from this one end 11 in the same direction as the sharp end of the needle 7, and the inner face of the ring 15 of the multi-function cap 5 has different radial sections SS (small), MM (medium), DD (deep) (see FIG. 11) that project at different distances away from an average plane parallel to this ring 15.

Figure 11:
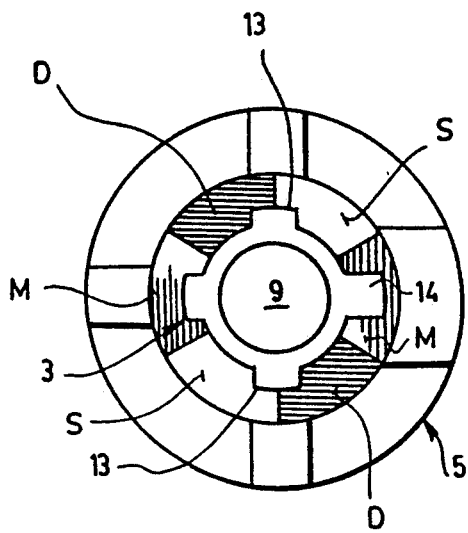
FIGS. 11 to 13 are bottom, side-elevational and top plan views of the combined lancet and multi-function cap shown in FIGS. 1 to 3, the side elevational view having cut-away portions.

As shown in FIG. 11, the different radial sections SS, MM, DD consist of a plurality of radially symmetrical steps of different heights. These radial sections may however be of different shape and consist, for example, of a pair of opposite, continuous surfaces of helical shape.

With such a structure, proper adjustment of the position of the multi-function cap 5 by rotation of the same about the mouth 53 of the injector device 51 relative to the lancet 3, allows the radially extending section 33 projecting from the one end 11 of the body 9 to be brought into alignment with any selected corresponding radial sections, say MM, of the inner face of the ring 15 and thus to control the depth of penetration of the lancet 3.

To ensure proper positioning of the lancet 3 within the lancet holder 59 of the lancet injector 51 and thus proper adjustment of the position of the multi-function cap 5 relative to the lancet 3, the elongated body 9 preferably has several longitudinal ribs 13, at least one of which, numbered 14, is sized and positioned to act also as a key for radially securing the body 9 within the lancet holder. One of the legs 19 of the cap 5, numbered 20, is also shaped and devised to cooperate with marks 35 externally made on the lancet injector 51 (see FIG. 5) in order to give a visible indication of the position of the cap 5 relative to the lancet 3 keyed in the lancet injector 51, and thus of the depth of penetration that will be achieved when operating the injector.

Thus, depth regulation can be easily achieved by appropriately setting the relative radial angular relationship between the truncated section 33 of the lancet 3, which has a substantially rectangular end face, and the inner face (or "metering face") of the multi-function cap 5 which is stepped in six segments SS, MM and DD. The increasing depths of shading shown in FIG. 11 indicates the increasing depths of the segments which are made of three pairs each positioned at a relative angle 180 degrees. The S-S pair are the shallowest the M-M pair the medium and the D-D pair the deepest.

The projecting key 14 provided on the body of the lancet 3, makes it possible to locate the lancet 3 in a constant position within the lancet holder 59 (see FIG. 9a) which is equipped with a matching key slot. Rotation of the cap 5 to the different radial positions S-S, M-M or D-D which are spaced at 60 degree intervals, causes the different height steps of the metering face to be brought into alignment with the truncated section 33 of the lancet 3 prior to impact. At impact, the depth of penetration of the needle 7 is determined by the segments of the metering face 29 that have been selected.

Such a rotation of the multi-function cap 5 held by its legs into the groove 57 provided on the external surface of the sleeve 55 can be facilitated by providing the peripheral surface of the ring 15 with a gripping knurled rim 37. The marks 35 made on the sleeve 55 adjacent the groove 57 give, in practice, a comfort depth scale. For the benefit of vision impaired and even completely blind users, tactile sensors may also be provided for each of the three indicated positions.

As aforesaid, the viewing window 30 allows the user to look right through the lancet injector 51 when it does not contain a lancet 3 that has been used. Vision is completely obscured if the device contains a used lancet 3 thus providing a clear indication that this used lancet should be immediately ejected.

While the drawings show a metering face comprised of three successive steps exclusively, many variations can be provided in this area without, in any way, departing from the scope of the invention. For instance, six or even twelve steps could be provided or as aforesaid, instead of any exact steps, the segmented radial areas showing FIG. 11 could be formed as a two start descending helical curve so as to provide continuously infinite variable degrees of penetration between the lower and upper limits i.e. within a 180 degree radial turn of the multi-function cap 5 relative to the lancet.

The other embodiment of combined lancet and multi-function cap 1' shown in FIGS. 4 and 14 to 16, is designed to work with any standard lancet injectors device already known and available. It comprises a lancet 3' of conventional structure which does not include any means for relative radial registration. As a result, penetration depth is not directly variable. Such a depth is however determined by the distance T between the inner and outer flat faces of the non-hooding type cap 5' (see FIG. 15).

In this embodiment, the plastic material of the lancet 3' and tip 5' may be given a colour corresponding to the thickness of the ring 15' of the tip 5', thereby making it possible to know the depth of penetration allowed by this ring 15' as a function of this colour and thus to determine whether this combined lancet and multi-function cap 1' is suitable for a given patient.

Of course, different tip 5' of distinguishable colours with other T dimensions may be provided to cater for other depths needed.

In another embodiment, one could employ a standard lancet slightly modified and to which would be added a truncated end 33 and a key 14, as disclosed hereinabove. In this case, the inner flat face of the cap could be changed into metering face while still using a basic non-hooding type cap, i.e. a cap with no locking legs 19.

Thus, one can see that four of the major features of the invention, i.e. isolation, depth control, hooding and combined lancet and multi-function cap, can be utilized in many combinations and permutations as needed, of which the foregoing are a few typical examples only, without in any manner departing from the scope of the invention.

Figure 9C:
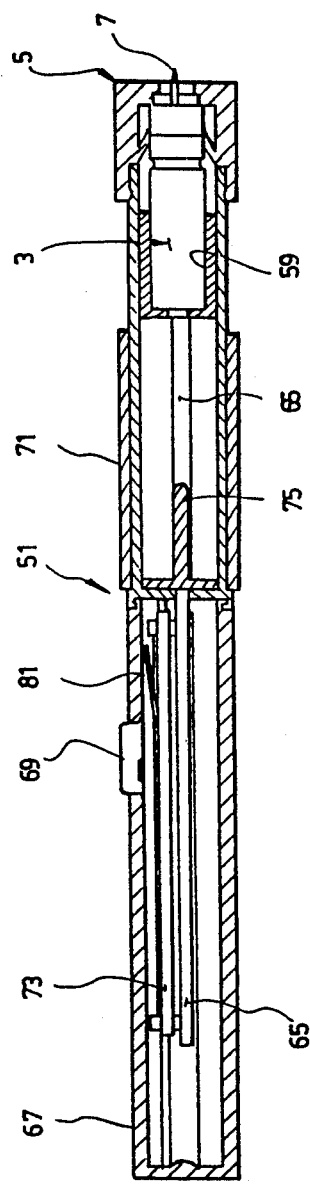
Figure 9E:
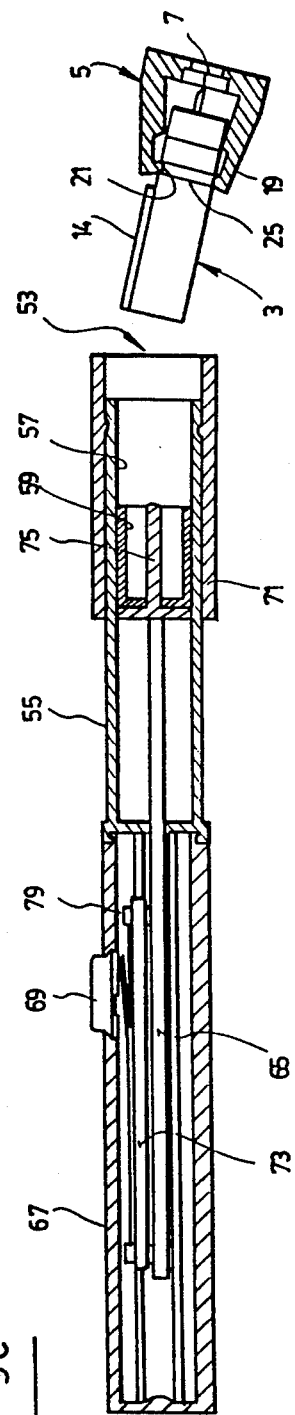
Figure 9D:
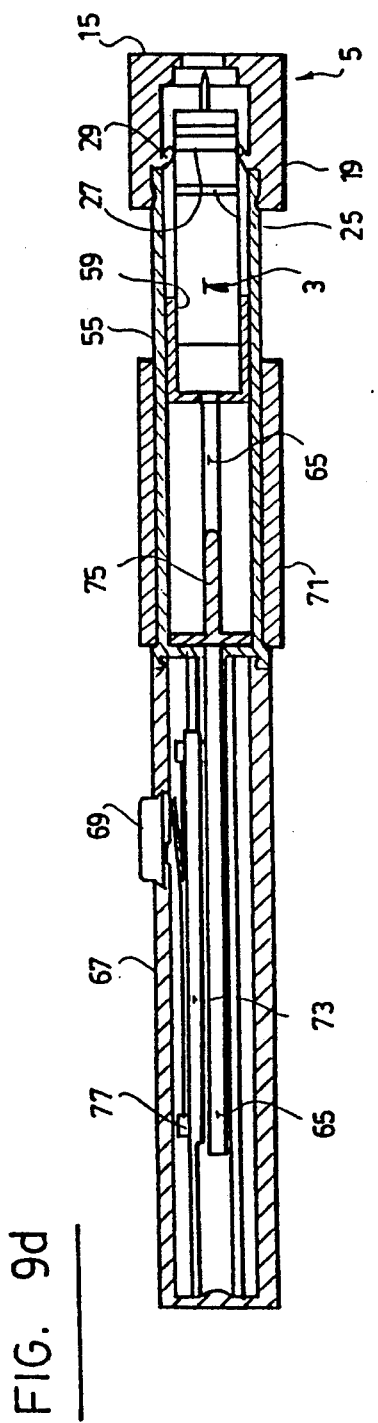

FIGS. 9a to 9c depict five typical sectional views of the assembled lancet injector 51 disclosed hereinabove, in the various sequential operating positions which are employed. FIG. 9a shows the loading position where the user inserts the lancet 3 into the lancet holder 59 with the key 14 serving to securely radially locate the lancet 3 in a key slot provided for this purpose in the lancet holder. The wings 61 which are integral with the lancet holder 59 make it possible for the user to hold the holder 59 while loading the lancet 3 the needle 7 of which is covered by the multi-function cap 5 which may subsequently be twisted off for use.

As shown in FIG. 9b, the multi-function cap 5, after having been twisted off, may then pushed onto the sleeve 55 where its legs 19 snap into the groove 57. In such a position, the multi-function cap 5 may be rotated to any desired indicated position on the comfort depth scale 35 (see FIG. 5).

To lock the device, the user pushes the wings 61 rearward in the slots 63 in the direction shown by arrow XI. Then, the injector 51 will take up the position shown in FIG. 9b wherein the shaft 65 in moving rearward has tensioned the elastomeric band 73 and said tension has been "locked" due to the self-tensioned detent 81 which has then dropped behind the detent stop 83.

FIG. 9c shows the lancet injector 51 after it has been fired by depressing the release button 69 which pushes the self-tensioned detent 81 out of the detent stop 83, thus releasing the stored tension on the shaft 65 and so causing the shaft to move rapidly forward and to assume the position showing FIG. 9c. The lancet 3 is thus rapidly propelled in the direction of arrow Y until such time as its motion is arrested due to the lancet 3 striking the metering inner face of the multi-function cap 5. The sharp end of the needle 7 then projects through the outer face of the multi-function cap 5 to the extent previously determined as above, thereby allowing it to penetrate the patient's skin accordingly, whereupon it instantly withdraws rearward in the direction of arrow X2 by virtue of the pressure exerted by elastomeric band 73 on the front pin 79, such pressure being generated by the inertia of the rapidly accelerated shaft 65 and all components carried thereon which at the time of penetration have caused it to overshoot its original position depicted in FIG. 9a. As the shaft 65 retracts, the lancet 3 is only permitted to partially retract as it is retained in a slightly forward position as depicted in FIG. 9d where the needle of the lancet 3 is held below the surface of the outer face of the multi-function cap 5 due to the retention leaves 29 which are angled so as to be easily deflected and thus by-passed on the forward stroke of lancet 3, but to be snapped on the rearward stroke into the retention groove 27, thereby inhibiting any further rearward movement of the lancet 3 and thus partially extracting this lancet from the lancet holder 59 which continues its rearward movement.

In this partially forward retained position, the lancet 3 completely obscures the viewing window 30, and thus provides the user with a ready means of determining whether a lancet remaining within the device has already been used.

The rapid withdrawal causes the shaft 65 to slightly overshoot its original position in the reverse direction as the rear pin 77 hits the elastomeric band 73 which acts as a mechanical shock absorber to protect the device from undue shock and consequential wear. The shaft 64 then continues to make a number of successive minor bi-lateral oscillations between the two extremities of elastomeric band 73 due to the alternate contact made with the band by the rear pin 77 and the front pin 79 as the energy stored within the device is smoothly dissipated.

The final stage whereby the lancet is ejected is shown in FIG. 9e. In this stage, the ejector 71 which rides on the sleeve 55 is pushed forward, thus advancing the ejector pins 75 which are an integral part of this ejector and pass through openings made in the rear end of lancet holder 59 to push the lancet 3, to eject it and to advance it further into the multi-function cap 5. The forward end of ejector 71 then commences to dislodge the locking ends 21 of the legs 19 of the cap 5 from the groove 57 of the sleeve 55 so as to eject both the lancet 3 and the tip 5 in concert with the locking ends 21 then firmly engaging into the locking groove 25 of the lancet 3. The two assembled components with the lancet needle 7 securely hooded and locked, then fall away from the injector 51.

When used with the alternative non-hooding type multi-function cap 5' and a standard lancet 3' as showing FIG. 4 and 14 to 16, the two components are still ejected almost simultaneously but unassembled.

What is claimed is:

1. A combined lancet and multi-function cap, comprising:

a lancet including a needle having a sharp end, and an elongated body of plastic material embedding said needle except for its sharp end that projects from one end of said body over a given length, said elongated body having at least one longitudinal rib; and a cap also made of plastic material, said cap being detachably mounted on said one end of said body to cover the sharp end of said needle and keep it sterile until the lancet is used, wherein said cap is a multi-function cap and comprises:

a ring having an inner face, an outer face and a central opening sized to let pass the sharp end of said needle but not the one end of the body of the lancet, said ring having such a thickness and a shape as to let pass the sharp end of the needle through the central opening and penetrate the skin of a patient's finger in contact with the outer face of the ring, and means projecting from the inner face of said ring for use to properly position the ring with respect to a lancet injector having a mouth through which said lancet may be inserted and subsequently projected out, in such a manner that the central opening of said ring is aligned with the sharp end of said needle, whereby when the multi-function cap is detached from said lancet and is connected to said lancet injector, the ring of said tip extends across said mouth and positively controls the depth of penetration of said lancet in the patient' skin, said lancet and multi-function cap being made of the same plastic material and together forming an integral structure in which is embedded said needle, with the body of said lancet radially projecting from the ring of said multi-function cap, said body and ring being integrally connected by a very short stem of reduced diameter that is coaxial to said needle and sized to make said tip easily detachable from said body by twisting and pulling to release said sharp end, said means for use to properly position the ring with respect to the lancet injector including at least three legs integral to and symmetrically positioned around said ring, said legs projecting from said ring in the direction of the inner face of said ring and having resilient ends snappable into a groove provided for this purpose on said lancet injector near the mouth of said injector; and the body of said lancet also comprising a first peripheral groove that extends parallel to the one end of said body and is sized to be snapped by the resilient ends of said at least three legs, said first peripheral groove being positioned along said body in such a manner that when the resilient ends of said at least three legs are snapped into said first groove, the ring of the multi-function cap extends past and over the sharp end of the needle projecting from the one end of the body of the lancet, thereby preventing accidental finger-sticks with said sharp end.

2. The combined lancet and multi-function cap of claim 1, wherein:

the body of said lancet comprises a second peripheral groove extending parallel to the first groove between said first groove and the one end of said body; and each of said at least three legs of the multi-function cap comprises a small restraining leaf projecting towards the center of the central opening of the ring of said cap, said leaves being of such a length as to engage and lock into the second groove of said body to prevent said lancet from moving out from said multi-function cap after said lancet has been projected toward the inner face of said ring and has bounded back at a safe distance where the sharp end of the needle does not project anymore from the outer face of said ring.

3. The combined lancet and multi-function cap of claim 2, wherein:

said multi-function cap comprises at least one aperture acting as a viewing window to make it possible for someone to check whether the lancet is engaged and locked by the restraining leaves, such an engagement being indicative of the fact that the lancet has been used once and is to be discarded.

4. The combined lancet and multi-function cap of claim 1, wherein:

the one end of the body of said lancet has at least one radially extending section that projects from said one end in the same direction as the sharp end of the needle; and the inner face of the ring of said multi-function cap has different radial sections that project at different distances away from an average plane parallel to said ring, whereby proper adjustment of the position of the multi-function cap by rotation of the same about the mouth of the lancet injector relative to the lancet allows said at least one radially extending section projecting from the one end of the body to be brought into alignment with any selected corresponding radical section of the inner face of the ring and thus to control the depth of penetration of said lancet.

5. The combined lancet and multi-function cap of claim 4, wherein:

said elongated body has several longitudinal ribs including said at least one longitudinal rib, at least one of said ribs is sized and positioned to act also as a key for radially securing the body within said lancet injector whenever such a device is used; and one of said legs of said multi-function cap is shaped and devised to cooperate with marks externally made on the lancet injector in order to give a visible indication of the position of the multi-function cap relative to the lancet keyed in said lancet injector, and thus of the depth of penetration that will be achieved by operating said injector.

6. The combined lancet and multi-function cap of claim 5, wherein the different radial sections that project from the inner face of the ring, consist of a plurality of steps of different heights.

7. The combined lancet and multi-function cap of claim 5, wherein the different radial sections that project from the inner face of the ring, consist of a continuous surface of helical shape.

8. The combined lancet and multi-function cap of claim 5, wherein:
the body of said lancet comprises a second peripheral groove extending parallel to the first groove between said first groove and the one end of said body; and
each of said at least three legs of the multi-function cap comprises a small restraining leaf projecting towards the center of the central opening of the ring of said cap, said leaves being a of such a length as to engage and lock into the second groove of said body to prevent said lancet from moving out from said multi-function cap after said lancet has been projected toward the inner face of said ring and has bounced back at a safe distance where the sharp end of the needle does not project anymore from the outer face of said ring.

9. The combined lancet and multi-function cap of claim 8, wherein:
said multi-function cap comprises at least one aperture acting as a viewing window to make it possible for someone to check whether the lancet is engaged and locked by the restraining leaves, such as engagement being indicative of the fact that the lancet has been used once and is to be discarded.

10. The combination of a lancet injector with a combined lancet and multi-function cap of claim 9 wherein said lancet injector comprises:
a lancet receiving sleeve having a longitudinal axis and a mouth at one end through which said lancet may be inserted and subsequently projected out;
a lancet holder slidably mounted within said sleeve, said holder being sized and shaped to receive said lancet and to cooperate with said at least one longitudinal rib of said lancet to prevent it from rotating about said longitudinal axis;
means to prevent the lancet holder from rotating within the lancet receiving sleeve said means comprising a pair of gripping wings radially projecting from said lancet holder and slidably engaged within longitudinal slots provided for this purpose within said sleeve, said gripping wings projecting radially outwardly from said sleeve through said longitudinal slots;
a central shaft integrally projecting from said lancet holder in a direction opposite to said mouth, said central shaft being coaxial with said longitudinal axis and projecting out of said lancet receiving sleeve;
elastic means mounted in a housing connected to said lancet receiving sleeve opposite the mouth thereof to project forward the central shaft and lancet holder upon pressing of a release button externally mounted on said housing, said elastic means being energized while the release button is triggered in operative position every time the lancet holder is manually moved within said sleeve by said gripping winds; and
a sleeve-shaped ejector slidably mounted externally onto the lancet receiving sleeve, said ejector having longitudinally slots positioned to make it movable without being stopped by the gripping wings and means to engage the lancet with the lancet holder and being manually movable toward the mouth of the lancet receiving sleeve to push the lancet out of the lancet holder and to detach and throw out the multi-function cap connected and locked thereto without having to put the fingers on said cap to remove the used lancet from the lancet injector.

11. The combination of claim 10, wherein said elastic means comprises:
an elastomeric band held under slight tension by four points so as to form an elongated rectangle having two small sides and main axis points coaxial with said longitudinal axis and said central shaft;
a front pin and a rear pin radially projecting from said central shaft in such a manner as to respectively contact the small sides of the rectangle formed by said elastomeric band within said rectangle;
a self-tensioned detent integral to said central shaft, said detent projecting radially outwardly; and
a stop positioned onto said housing in such a manner as to extent across the detent and lock the central shaft in a rearward position where the rear pin of the central shaft presses against the elastomeric band and is biased by the same and the lancet holder extends within said lancet receiving sleeve away from said mouth, and;
said release button being positioned onto the housing so as to push said detent away from said stop whenever desired;
whereby pushing by said release button of said detent causes the central shaft, the lancet holder and the lancet mounted therein to be projected forward toward the mouth of the sleeve, and then to be pulled back by action of the elastomeric band onto the front pin, thereby causing very rapid skin perforation and speedy withdrawal of the needle.

12. The combination of a lancet injector with a combined lancet and multi-function cap of claim 5 wherein said lancet injector comprises:
a lancet receiving sleeve having a longitudinal axis and a mouth at one end through which said lancet may be inserted and subsequently projected out;
a lancet holder slidably mounted within said sleeve, said holder being sized and shaped to receive said lancet and to cooperate with said at least one longitudinal rib of said lancet to prevent it from rotating about said longitudinal axis;
means to prevent the lancet holder from rotating within the lancet receiving sleeve, said means comprising a pair of gripping wings radially projecting from said lancet holder and slidably engaged within longitudinal slots provided for this purpose within said sleeve, said gripping wings projecting radially outwardly from said sleeve through said longitudinal slots;
a central shaft integrally projecting from said lancet holder in a direction opposite to said mouth, said central shaft being coaxial with said longitudinal axis and projecting out of said lancet receiving sleeve;
elastic means mounted in a housing connected to said lancet receiving sleeve opposite the mouth thereof to project forward the central shaft and lancet holder upon pressing of a release button externally mounted on said housing, said elastic means being energized while the release button is triggered in operative position every time the lancet holder is manually moved within said sleeve by said gripping winds; and a sleeve-shaped ejector slidably mounted externally onto the lancet receiving sleeve, said ejector having longitudinal slots positioned to make it movable without being stopped by the gripping wings and means to engage the lancet with the lancet holder and being manually movable toward the mouth of the lancet receiving sleeve to push the lancet out of the lancet holder and to detach and throw out the multi-function cap connected and locked thereto without having to put the fingers on said cap to remove the used lancet from the lancet injector.

13. The combination of claim 12, wherein said elastic means comprises:

an elastomeric band held under slight tension by four points so as to form an elongated rectangle having two small sides and main axis points coaxial with said longitudinal axis and said central shaft;

a front pin and a rear pin radially projecting from said central shaft in such a manner as to respectively contact the small sides of the rectangle formed by said elastomeric band within said rectangle;

a self-tensioned detent integral to said central shaft, said detent projecting radially outwardly; and a stop positioned onto said housing in such a manner as to extent across the detent and lock the central shaft in a rearward position where the rear pin of the central shaft presses against the elastomeric band and is biased by the same and the lancet holder extends within said lancet receiving sleeve away from said mouth, and;

said release button being positioned onto the housing so as to push said detent away from said stop whenever desired;

whereby pushing by said release button of said detent causes the central shaft, the lancet holder and the lancet mounted therein to be projected forward toward the mouth of the sleeve, and then to be pulled back by action of the elastomeric band onto the front pin, thereby causing very rapid skin perforation and speedy withdrawal of the needle.

14. The combination of a lancet injector with a combined lancet and multi-function cap of claim 1 wherein said lancet injector comprises:

a lancet receiving sleeve having a longitudinal axis and a mouth at one end through which said lancet may be inserted and subsequently projected out;

a lancet holder slidably mounted within said sleeve, said holder being sized and shaped to receive said lancet and to cooperate with said at least one longitudinal rib of said lancet to prevent it from rotating about said longitudinal axis;

means to prevent the lancet holder from rotating within the lancet receiving sleeve, said means comprising a pair of gripping wings radially projecting from said lancet holder and slidably engaged within longitudinal slots provided for this purpose within said sleeve, said gripping wings projecting radially outwardly from said sleeve through said longitudinal slots;

a central shaft integrally projecting from said lancet holder in a direction opposite to said mouth, said central shaft being coaxial with said longitudinal axis and projecting out of said receiving sleeve;

elastic means mounted in a housing connected to said lancet receiving sleeve opposite the mouth thereof to project forward the central shaft and lancet holder upon pressing of a release button externally mounted on said housing, said elastic means being energized while the release button is triggered in operative position every time the lancet holder is manually moved within said sleeve by said gripping winds; and a sleeve-shaped ejector slidably mounted externally onto the lancet receiving sleeve, said ejector having longitudinally slots positioned to make it movable without being stopped by the gripping wings and means to engage the lancet with the lancet holder and being manually movable toward the mouth of the lancet receiving sleeve to push the lancet out of the lancet holder and to detach and throw out the multi-function cap connected and locked thereto without having to put the fingers on said cap to remove the used lancet from the lancet injector.

15. The combination of claim 14, wherein said elastic means comprises:

an elastomeric band held under slight tension by four points so as to form an elongated rectangle having two small sides and main axis points coaxial with said longitudinal axis and said central shaft;

a front pin and a rear pin radially projecting from said central shaft in such a manner as to respectively contact the small sides of the rectangle formed by said elastomeric band within said rectangle;

a self-tensioned detent integral to said central shaft, said detent projecting radially outwardly; and a stop positioned onto said housing in such a manner as to extent across the detent and lock the central shaft in a rearward position where the rear pin of the central shaft presses against the elastomeric band and is biased by the same and the lancet holder extends within said lancet receiving sleeve away from said mouth, and;

said release button being positioned onto the housing so as to push said detent away from said stop whenever desired;

whereby pushing by said release button of said detent causes the central shaft, the lancet holder and the lancet mounted therein to be projected forward toward the mouth of the sleeve, and then to be pulled back by action of the elastomeric band onto the front pin, thereby causing very rapid skin perforation and speedy withdrawal of the needle.

16. The combination of a lancet injector with a combined lancet and multi-function cap comprising:

a) a lancet including a needle having a sharp end, and an elongated body of plastic material embedding said needle except for its sharp end that projects from one end of said body over a given length, said elongated body having at least one longitudinal rib; and b) a cap also made of plastic material, said cap being detachably mounted on said one end of said body to cover the sharp end of said needle and keep it sterile until the lancet is used, wherein said cap is a multi-function cap and comprises:

a ring having an inner face, an outer face and a central opening sized to let pass the sharp end of said needle but not the one end of the body of the lancet, said ring having such a thickness and a shape as to let pass the sharp end of the needle through the central opening and penetrate the skin of a patient's finger in contact with the outer face of the ring, and means projecting from the inner face of said ring for use to properly position the ring with respect to a lancet injector having a mouth through which said lancet may be inserted and subsequently projected out, in such a manner that the central opening of said ring is aligned with the sharp end of said needle, whereby when the multi-function cap is detached from said lancet and is connected to said lancet injector, the ring of said tip extends across said mouth and positively controls the depth of penetration of said lancet in the patient' skin, a lancet receiving sleeve having a longitudinal axis and a mouth at one end through which said lancet may be inserted and subsequently projected out;

a lancet holder slidably mounted within said sleeve, said holder being sized and shaped to receive said lancet and to cooperate with said at least one longitudinal rib of said lancet to prevent it from rotating about said longitudinal axis;

means to prevent the lancet holder from rotating within the lancet receiving sleeve, said means comprising a pair of gripping wings radially projecting from said lancet holder and slidably engaged within longitudinal slots provided for this purpose within said sleeve, said gripping wings projecting radially outwardly from said sleeve through said longitudinal slots;

a central shaft integrally projecting from said lancet holder in a direction opposite to said mouth, said central shaft being coaxial with said longitudinal axis and projecting out of said lancet receiving sleeve;

elastic means mounted in a housing connected to said lancet receiving sleeve opposite the mouth thereof to project forward the central shaft and lancet holder upon pressing of a release button externally mounted on said housing, said elastic means being energized while the release button is triggered in operative position every time the lancet holder is manually moved within said sleeve by said gripping winds; and a sleeve-shaped ejector slidably mounted externally onto the lancet receiving sleeve, said ejector having longitudinally slots positioned to make it movable without being stopped by the gripping wings and means to engage the lancet with the lancet holder and being manually movable toward the mouth of the lancet receiving sleeve to push the lancet out of the lancet holder and to detach and throw out the multi-function cap connected and locked thereto without having to put the fingers on said cap to remove the used lancet from the lancet injector.

17. The combination of claim 16, wherein said elastic means comprises:

an elastomeric band held under slight tension by four points so as to form an elongated rectangle having two small sides and main axis points coaxial with said longitudinal axis and said central shaft;

a front pin and a rear pin radially projecting from said central shaft in such a manner as to respectively contact the small sides of the rectangle formed by said elastomeric band within said rectangle;

a self-tensioned detent integral to said central shaft, said detent projecting radially outwardly; and a stop positioned onto said housing in such a manner as to extent across the detent and lock the central shaft in a rearward position where the rear pin of the central shaft presses against the elastomeric band and is biased by the same and the lancet holder extends within said lancet receiving sleeve away from said mouth, and;

said release button being positioned onto the housing so as to push said detent away from said stop whenever desired;

whereby pushing by said release button of said detent causes the central shaft, the lancet holder and the lancet mounted therein to be projected forward toward the mouth of the sleeve, and then to be pulled back by action of the elastomeric band onto the front pin, thereby causing very rapid skin perforation and speedy withdrawal of the needle.

18. The combination of a lancet injector with a combined lancet and multi-function cap comprising:

a) a lancet including a needle having a sharp end, and an elongated body of plastic material embedding said needle except for its sharp end that projects from one end of said body over a given length, said elongated body having at least one longitudinal rib; and b) a cap also made of plastic material, said cap being detachably mounted on said one end of said body to cover the sharp end of said needle and keep it sterile until the lancet is used, wherein said cap is a multi-function cap and comprises:

a ring having an inner face, an outer face and a central opening sized to let pass the sharp end of said needle but not the one end of the body of the lancet, said ring having such a thickness and a shape as to let pass the sharp end of the needle through the central opening and penetrate the skin of a patient's finger in contact with the outer face of the ring, and means projecting from the inner face of said ring for use to properly position the ring with respect to a lancet injector having a mouth through which said lancet may be inserted and subsequently projected out, in such a manner that the central opening of said ring is aligned with the sharp end of said needle, whereby when the multi-function cap is detached from said lancet and is connected to said lancet injector, the ring of said tip extends across said mouth and positively controls the depth of penetration of said lancet in the patient's skin, and said lancet and multi-function cap being made of the same plastic material and together forming an integral structure in which is embedded said needle, with the body of said lancet radially projecting from the ring of said multi-function cap, said body and ring being integrally connected by a very short stem of reduced diameter that is coaxial to said needle and sized to make said tip easily detachable from said body by twisting and pulling to release said sharp end, said means for use to properly position the ring with respect to the lancet injector consisting of a peripheral skirt integral to and projecting from said ring in the direction of the inner face of said ring, said skirt being sized and shaped to fit onto the mouth of the lancet injector and thus allow connection of said ring to said lancet injector across said mouth, said plastic material of which said lancet and cap are made, having color corresponding to the thickness of the ring of the cap, thereby making it possible to know the depth of penetration allowed by said ring as a function of said color and thus to determine whether said combined lancet and multi-function cap is suitable for a given patient, a lancet receiving sleeve having a longitudinal axis and a mouth at one end through which said lancet may be inserted and subsequently projected out;

a lancet holder slidably mounted within said sleeve, said holder being sized and shaped to receive said lancet and to cooperate with said at least one longitudinal rib of said lancet to prevent it from rotating about said longitudinal axis;

means to prevent the lancet holder from rotating within the lancet receiving sleeve, said means comprising a pair of gripping wings radially projecting from said lancet holder and slidably engaged within longitudinal slots provided for this purpose within said sleeve, said gripping wings projecting radially outwardly from said sleeve through said longitudinal slots;

a central shaft integrally projecting from said lancet holder in a direction opposite to said mouth, said central shaft being coaxial with said longitudinal axis and projecting out of said lancet receiving sleeve;

elastic means mounted in a housing connected to said lancet receiving sleeve opposite the mouth thereof to project forward the central shaft and lancet holder upon pressing of a release button externally mounted on said housing, said elastic means being energized while the release button is triggered in operative position every time the lancet holder is manually moved within said sleeve by said gripping winds; and a sleeve-shaped ejector slidably mounted externally onto the lancet receiving sleeve, said ejector having longitudinally slots positioned to make it movable without being stopped by the gripping wings and means to engage the lancet with the lancet holder and being manually movable toward the mouth of the lancet receiving sleeve to push the lancet out of the lancet holder and to detach and throw out the multi-function cap connected and locked thereto without having to put fingers on said cap to remove the used lancet from the lancet injector.

19. The combination of claim 18, wherein said elastic means comprises:

an elastomeric band held under slight tension by four points so as to form an elongated rectangle having two small sides and main axis points coaxial with said longitudinal axis and said central shaft;

a front pin and a rear pin radially projecting from said central shaft in such a manner as to respectively contact the small sides of the rectangle formed by said elastomeric band within said rectangle;

a self-tensioned detent integral to said central shaft, said detent projecting radially outwardly; and a stop positioned onto said housing in such a manner as to extent across the detent and lock the central shaft in a rearward position where the rear pin of the central shaft presses against the elastomeric band and is biased by the same and the lancet holder extends within said lancet receiving sleeve away from said mouth, and;

said release button being positioned onto the housing so as to push said detent away from said stop whenever desired;

whereby pushing by said release button of said detent causes the central shaft the lancet holder and the lancet mounted therein to be projected forward toward the mouth of the sleeve, and then to be pulled back by action of the elastomeric band onto the front pin, thereby causing very rapid skin perforation and speedy withdrawal of the needle.

* * * * *